(12) United States Patent
Otaki

(10) Patent No.: US 11,313,812 B2
(45) Date of Patent: Apr. 26, 2022

(54) RADIATION DETECTOR

(71) Applicant: Konica Minolta, Inc., Tokyo (JP)

(72) Inventor: Junichiro Otaki, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 35 days.

(21) Appl. No.: 17/072,419

(22) Filed: Oct. 16, 2020

(65) Prior Publication Data

US 2021/0148838 A1 May 20, 2021

(30) Foreign Application Priority Data

Nov. 15, 2019 (JP) .............................. JP2019-206637

(51) Int. Cl.
*G03B 42/04* (2021.01)
*G01N 23/04* (2018.01)
*G01N 23/06* (2018.01)
*A61B 6/00* (2006.01)

(52) U.S. Cl.
CPC .............. *G01N 23/04* (2013.01); *A61B 6/44* (2013.01); *G01N 23/06* (2013.01); *G01N 2223/04* (2013.01); *G01N 2223/30* (2013.01); *G01N 2223/40* (2013.01)

(58) Field of Classification Search
CPC ........ G01N 23/00; G01N 23/04; G01N 23/06; G01N 2223/30; G01N 2223/04; G01N 2223/40; A61B 6/00; A61B 6/44; A61B 6/4233; G01T 1/244; G03B 42/04
See application file for complete search history.

(56) References Cited

FOREIGN PATENT DOCUMENTS

JP 2010-282155 A 12/2010
WO 2017/145444 A1 8/2017

*Primary Examiner* — Jurie Yun
(74) *Attorney, Agent, or Firm* — Lucas & Mercanti, LLP

(57) ABSTRACT

A radiation detector includes an image generator and a case. The image generator generates a radiograph according to received radiation. The case stores the image generator and includes a first component and a second component screwed to the first component. The second component is movable with respect to the first component in a direction along a seat surface of a screw by a screw hole of the second component being formed such that a diameter is larger than a diameter of a shaft of the screw but smaller than a diameter of a head of the screw. A loosening torque that acts, in a direction to loosen the screw, on the screw when the seat surface receives a frictional force from the second component is smaller than a loosening start torque that is the loosening torque of when the screw starts to loosen.

6 Claims, 12 Drawing Sheets

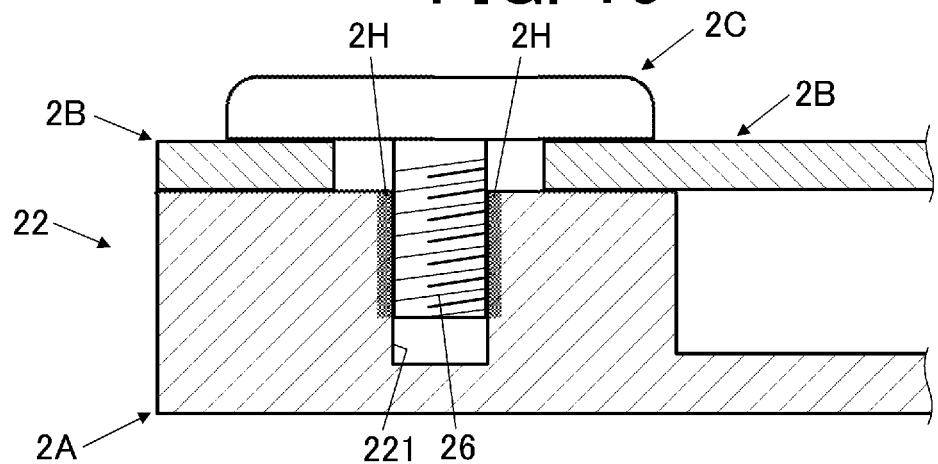
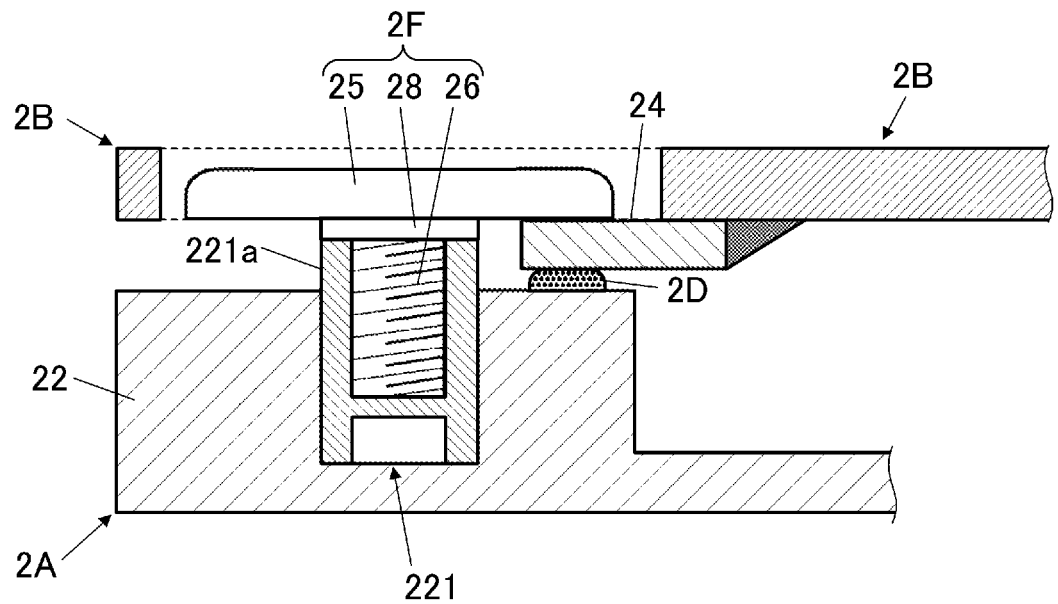

FIG. 19
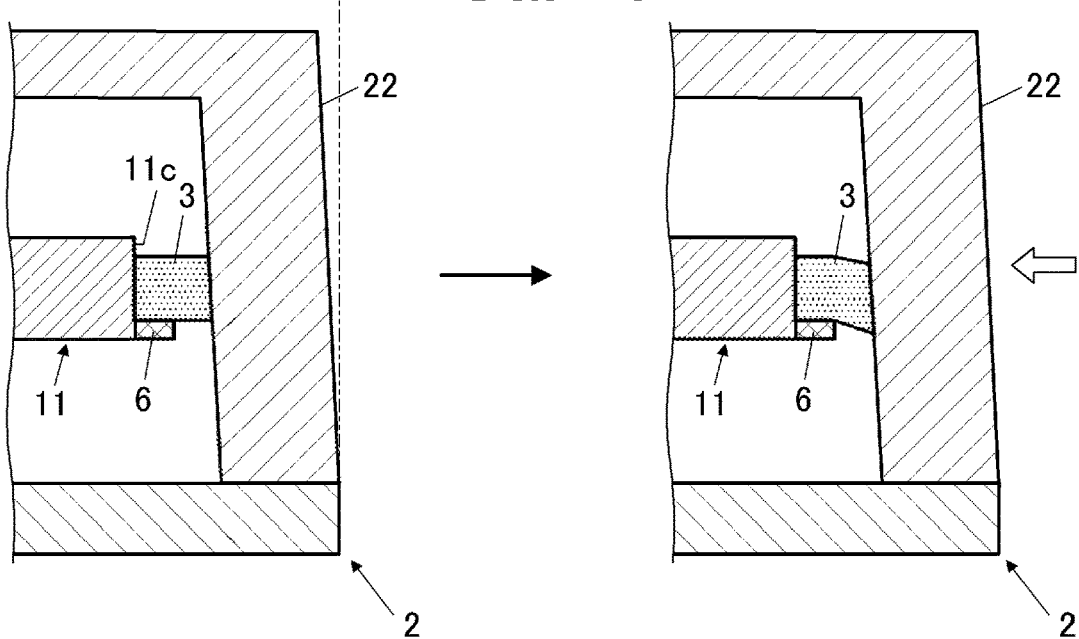
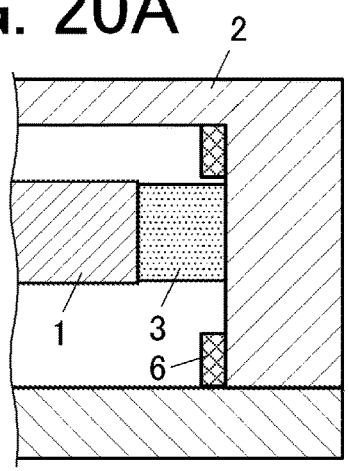
FIG. 20A
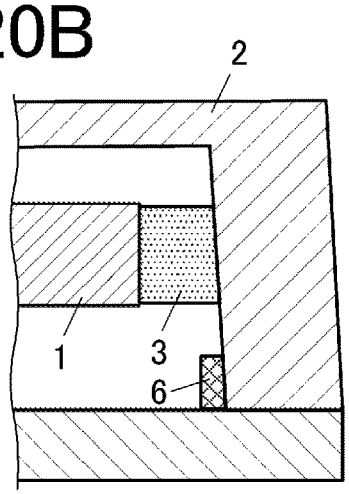
FIG. 20B
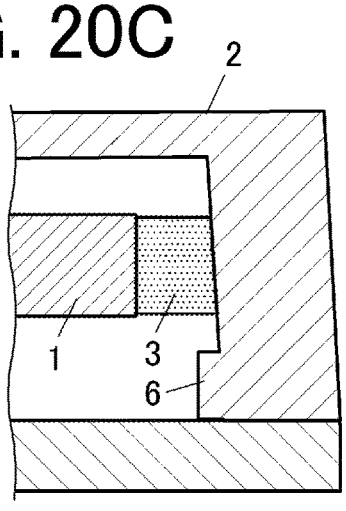
FIG. 20C
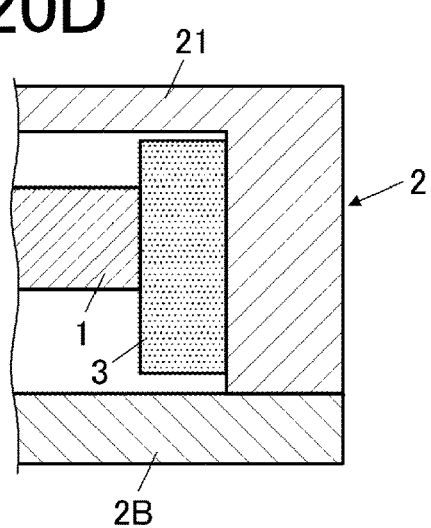
FIG. 20D

RADIATION DETECTOR

CROSS-REFERENCE TO RELATED APPLICATIONS

The entire disclosure of Japanese Patent Application No. 2019-206637 filed on Nov. 15, 2019 is incorporated herein by reference in its entirety.

BACKGROUND

Technological Field

The present disclosure relates to a radiation detector.

Description of the Related Art

In a panel-shaped radiation detector (Flat Panel Detector: FPD) including a case composed of a box (front plate) and a lid (back plate), once the lid adheres to the box, maintenance is difficult thereafter. Hence, conventionally, a case of a radiation detector has a structure in which a lid is fixed to a box with screws.

Examples of radiographic imaging using a panel-shaped radiation detector include a method of placing a radiation detector on a bed, laying an examinee thereon, and emitting radiation to the examinee from the above.

However, while the radiation incidence plane of a radiation detector is planar, the body of an examinee has many curved surfaces. Hence, the contact surface of an examinee and a radiation detector is small. An examinee lying on a radiation detector therefore receives pressure from the radiation detector on their contact surface concentratedly and feels pain sometimes.

Then, in the case having the structure in which a lid is screwed to a box, in order that the case bends to fit the figure of an examinee, the lid is made movable with respect to the box in a direction along their contact surface.

For example, in WO 2017/145444 A1, there is disclosed a portable radiographic image-capturing device including a sensor panel and a casing (case) that accommodates the sensor panel, wherein one of a front plate and a back plate of the casing has a side wall portion(s) provided vertically at the outer peripheral edge thereof, and the other is attached to an end face of the side wall portion of the one so as to be movable in a planar direction.

Further, in JP 2010-282155 A, there is disclosed an X-ray imaging apparatus including a detection unit that detects X-rays and a housing (case) that contains the detection unit, wherein the housing includes a first housing, a second housing and a plurality of connecting members that connect the first housing to the second housing, and the plurality of connecting members connect the first housing to the second housing so as to allow relative movement therebetween in a direction perpendicular to an irradiating direction of the X-rays.

SUMMARY

In a conventional radiation detector as disclosed in WO 2017/145444 A1 or JP 2010-282155 A, when a lid moves with respect to a box, a screw(s) receives frictional force from the lid.

At the time, if at least one of a seat surface of the screw and the surface of the lid is not uniform (has minute bumpiness, etc.), and there is a difference (variation) in distribution of normal force that the screw receives from the lid or in distribution of a friction coefficient between the seat surface of the screw and the surface of the lid, the frictional force that the screw receives from the lid may differ between one side and the other side of the shaft of the screw.

This difference in the frictional force is torque that acts in a screw rotating direction. Depending on on which side of the shaft the frictional force is larger, the difference may be "loosening torque" that acts in a screw loosening direction.

In the conventional radiation detector as disclosed in WO 2017/145444 A1 or JP 2010-282155 A, the screw may loosen by the loosening torque.

When the screw continues to loosen, the head of the screw protrudes from the surface of the lid, or the screw comes out. As a result, the following situations may occur: the protruding head of the screw catches an object or person therearound and scratches the object or person; the come-out screw adversely affects another device; and the come-out screw is accidentally swallowed by an examinee or the like and injures his/her health.

The present disclosure has been made in view of the above problems, and objects of the present disclosure include, in a radiation detector including a case having (i) a first component and (ii) a second component screwed to the first component and movable with respect to the first component in a direction along a seat surface(s) of a screw(s), making the screw less likely to loosen, which occurs with movement of the second component.

In order to achieve at least one of the abovementioned objects, according to an aspect of the present disclosure, there is provided a radiation detector including:

an image generator that generates a radiograph according to received radiation; and a case that stores the image generator and includes a first component and a second component screwed to the first component, wherein the second component is movable with respect to the first component in a direction along a seat surface of a screw by a screw hole of the second component being formed such that a diameter is larger than a diameter of a shaft of the screw but smaller than a diameter of a head of the screw, and wherein a loosening torque that acts, in a direction to loosen the screw, on the screw when the seat surface receives a frictional force from the second component is smaller than a loosening start torque that is the loosening torque of when the screw starts to loosen.

BRIEF DESCRIPTION OF THE DRAWINGS

The advantages and features provided by one or more embodiments of the present invention will become more fully understood from the detailed description given hereinbelow and the appended drawings that are given by way of illustration only, and thus are not intended as a definition of the limits of the present invention, wherein:

FIG. 15 is a cross-sectional view of an end of another example of the radiation detector according to the first embodiment cut in the thickness direction;

FIG. 16 is a cross-sectional view of an end of another example of the radiation detector according to the first embodiment cut in the thickness direction;

FIG. 19 shows cross-sectional views of an end of another example of the radiation detector according to the second embodiment cut in the thickness direction;

FIG. 20A is a cross-sectional view of an end of another example of the radiation detector according to the second embodiment cut in the thickness direction;

FIG. 20B is a cross-sectional view of an end of another example of the radiation detector according to the second embodiment cut in the thickness direction;

FIG. 20C is a cross-sectional view of an end of another example of the radiation detector according to the second embodiment cut in the thickness direction;

FIG. 20D is a cross-sectional view of an end of another example of the radiation detector according to the second embodiment cut in the thickness direction;

DETAILED DESCRIPTION OF EMBODIMENTS

1. First Embodiment

Hereinafter, a first embodiment of the present disclosure will be described with reference to FIG. 1 to FIG. 16.

However, the scope of the present invention is not limited to the embodiment below or illustrated examples.

[1-1. Schematic Configuration of Radiation Detector]

Figure 1:
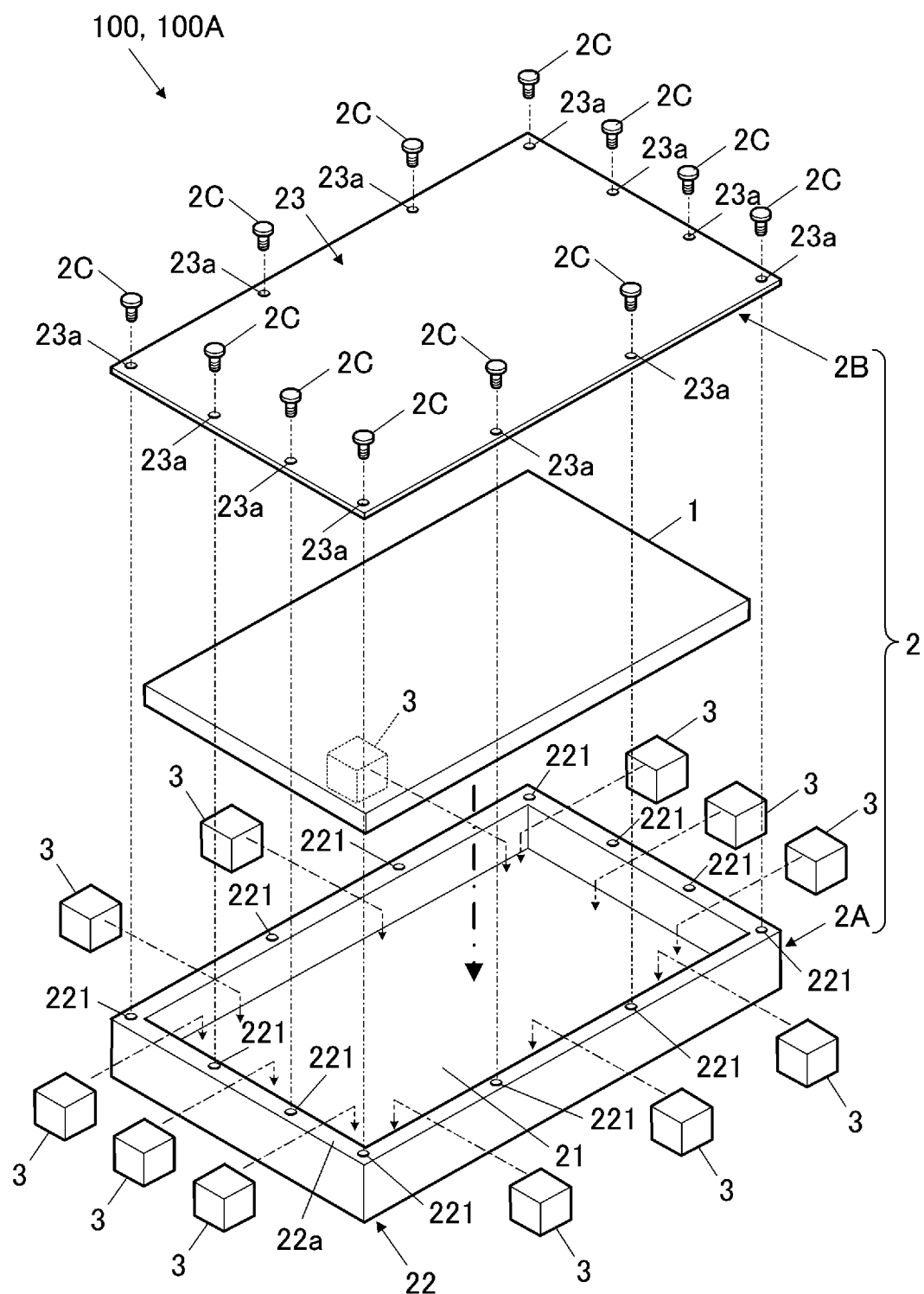
FIG. 1 is an exploded perspective view of a radiation detector according to a first embodiment and a second embodiment of the present disclosure.
Figure 2:
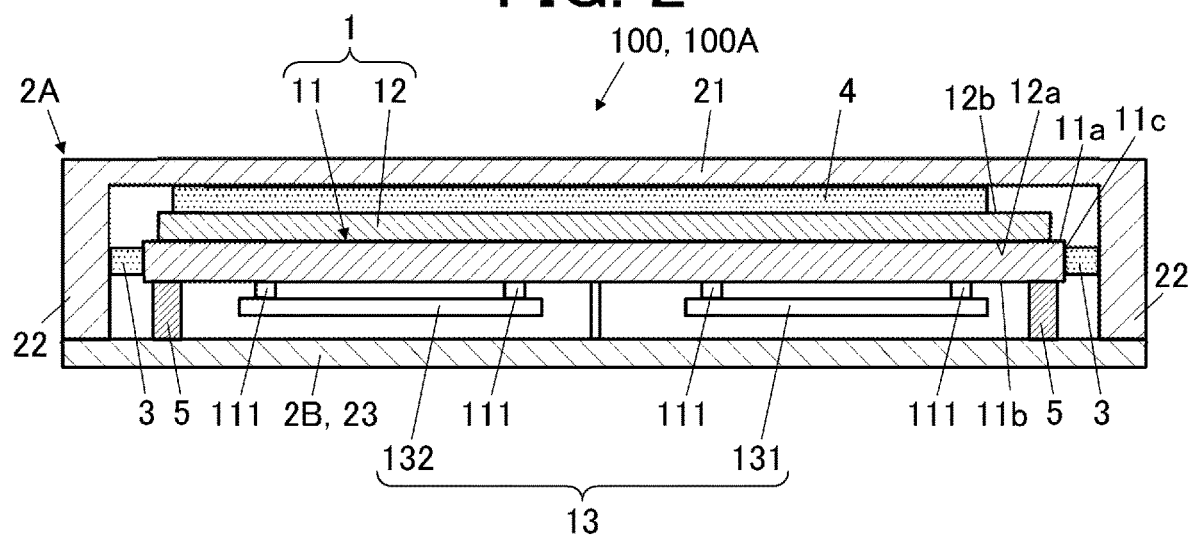
FIG. 2 is a cross-sectional view of the radiation detector according to the embodiments cut in the thickness direction.
Figure 3:
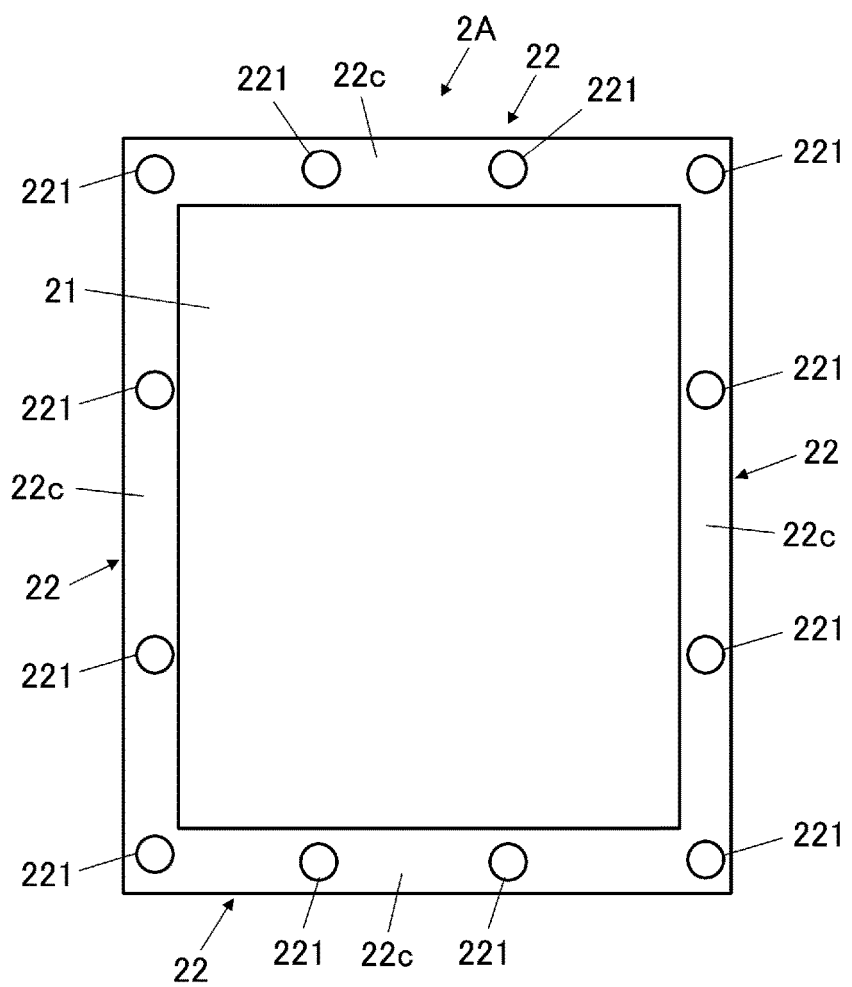
FIG. 3 is a plan view of a first component of the radiation detector according to the embodiments.
Figure 4:
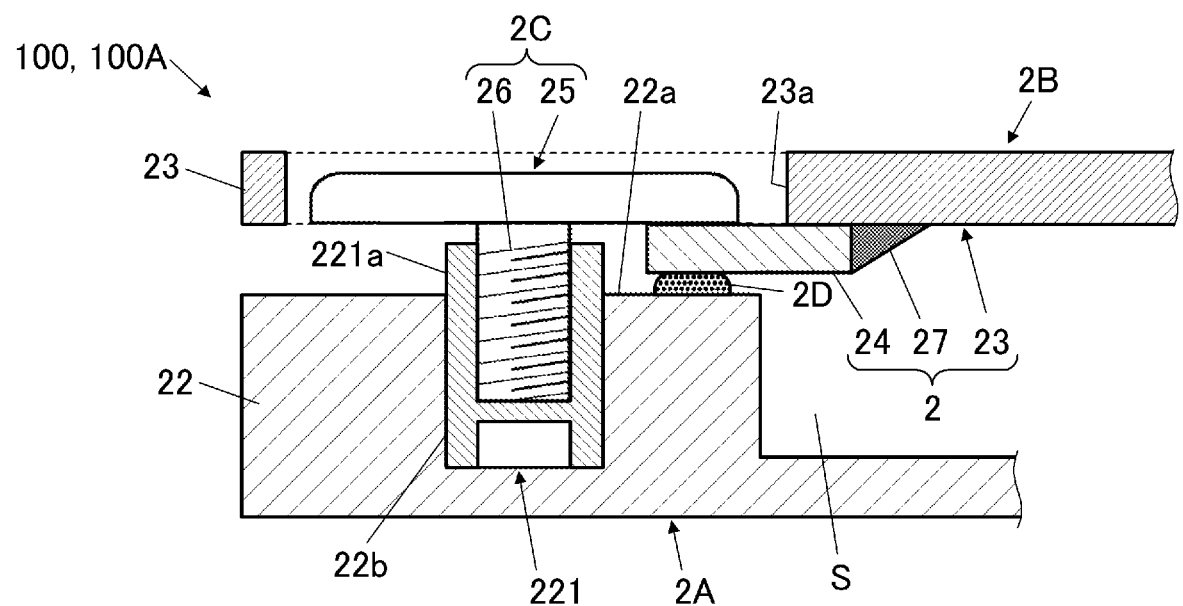
FIG. 4 is a cross-sectional view of the radiation detector according to the embodiments cut in the thickness direction.
Figure 5:
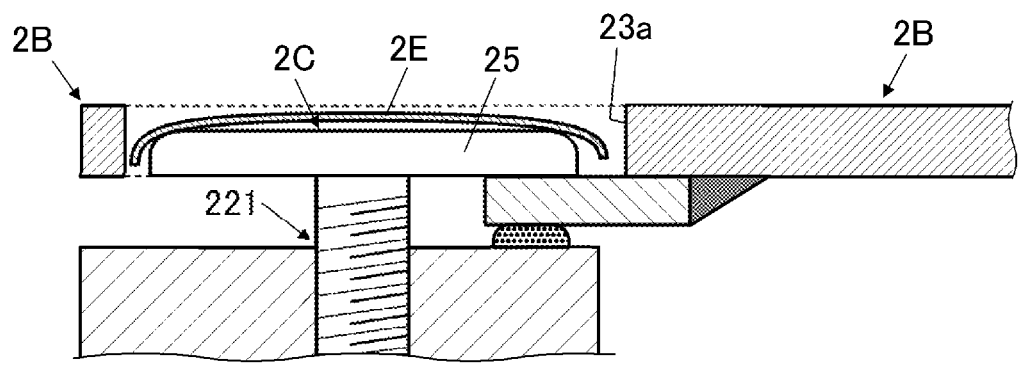
FIG. 5 is a cross-sectional view of an end of the radiation detector according to the embodiments cut in the thickness direction.
Figure 6:
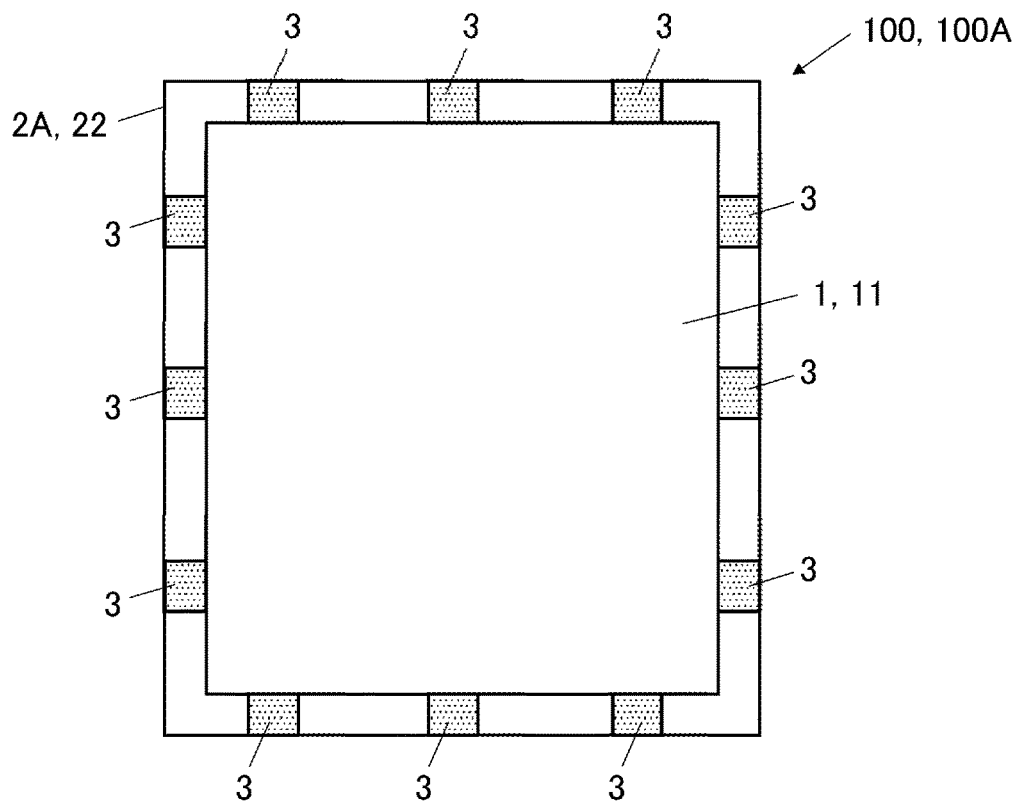
FIG. 6 is a plan view of the radiation detector with a second component thereof according to the embodiments removed.
Figure 7:
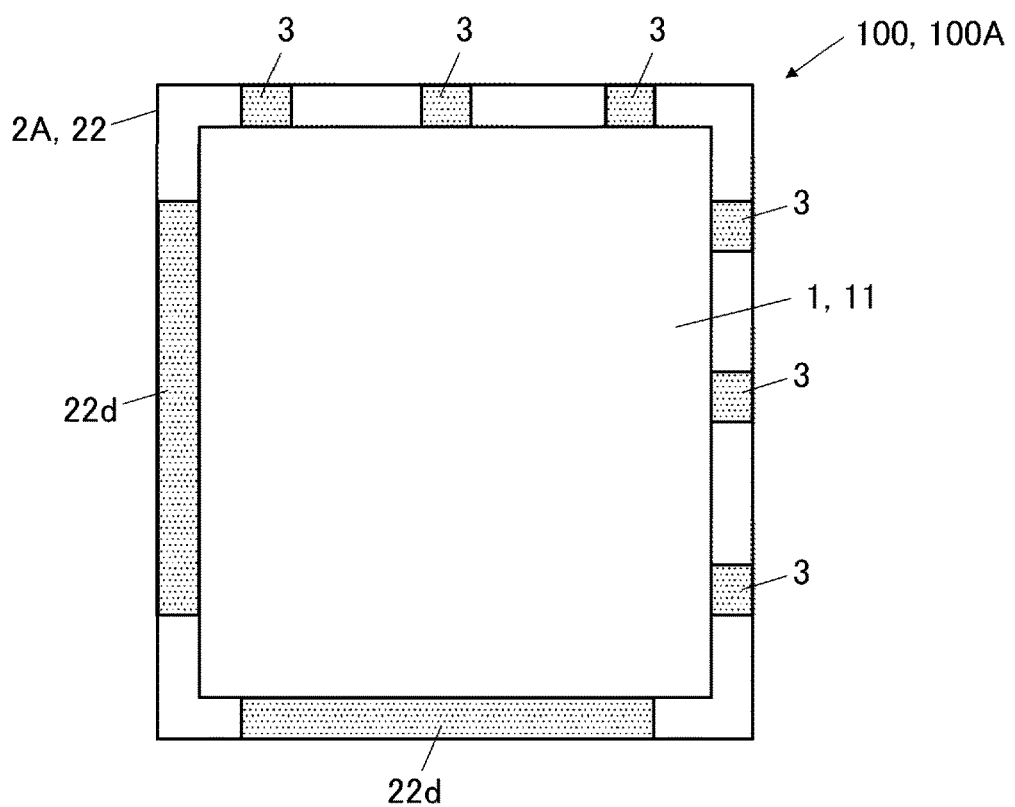
FIG. 7 is a plan view of the radiation detector with the second component according to a modification of the embodiments removed.

First, a schematic configuration of a radiation detector (hereinafter "detector 100") according to this embodiment will be described. FIG. 1 is an exploded perspective view of the detector 100. FIG. 2 is a cross-sectional view of the detector 100 cut in the thickness direction. FIG. 3 is a plan view of a first component of the detector 100. FIG. 4 and FIG. 5 are each a cross-sectional view of an end of the detector 100 cut in the thickness direction. FIG. 6 and FIG. 7 are each a plan view of the detector 100 with a second component thereof removed.

In the drawings, each reference sign after a comma may be a reference sign in a second embodiment, which will be described later.

As shown in FIG. 1, the detector 100 includes, for example, an image generator 1, a case 2 and a plurality of cushions 3.

[1-1-1. Image Generator]

As shown in FIG. 2, the image generator 1 includes, for example, a base 11 and a sensor panel 12.

The image generator 1 according to this embodiment further includes an electronic component 13.

The base 11 supports the sensor panel 12 and the electronic component 13.

The base 11 according to this embodiment is formed of a carbon fiber reinforced plastic (CFRP) resin so as to be a rectangular plate shape.

The base 11 may be formed of another material as needed.

The sensor panel 12 is disposed on a first face 11a of the base 11 and supported by the base 11.

The sensor panel 12 includes a substrate and a plurality of semiconductor elements.

The substrate according to this embodiment is rectangular in a front view and has substantially the same size as or one size smaller than the base 11.

The sensor panel 12 according to this embodiment includes switch elements (not shown) disposed near the semiconductor elements, scan lines and signal lines (not shown) connected to the switch elements, and bias lines (not shown) connected to the semiconductor elements.

The semiconductor elements are formed so as to be two-dimensionally distributed on a third face 12b of the sensor panel 12 opposite to a second face 12a of the sensor panel 12, the second face 12a being in contact with the first face 11a of the base 11.

The semiconductor elements according to this embodiment are disposed in a matrix.

The sensor panel 12 may be flexible by the substrate being formed of resin. This makes the sensor panel 12 less likely to be damaged even when the case 2 bends or receives an impact from the outside.

The electronic component 13 is disposed on a fourth face 11b of the base 11 opposite to the first face 11a.

The electronic component 13 includes an electric board 131, a battery 132 and wiring.

The electric board 131 includes a power supply circuit for applying voltage to the semiconductor elements, a scanning circuit for controlling the switch elements, a readout circuit for reading out electric charges as signal values, a communication circuit for outputting image data to another device, and a control circuit for controlling these circuits to generate image data.

As shown in FIG. 2, the electric board 131 according to this embodiment is attached to the base 11 via bosses 111.

The bosses 111 may be part of the base 11 or may be separate from the base 11

It is preferable that the bosses 111 be insulative.

The wiring is configured by, for example, a flexible printed circuit(s), and connects terminals of the scan lines, the signal lines and the bias lines disposed on the third face 12b of the sensor panel 12 to the circuits of the electric board 131.

The battery 132 is connected to the electric board 131 to supply power to the circuits of the electric board 131.

Instead of or in addition to the battery 132, the electronic component 13 may have a connector(s) (not shown) for receiving power from the outside.

The image generator 1 thus configured can generate a radiograph(s) according to received radiation.

[1-1-2. Case]

As shown in FIG. 1 and FIG. 2, the case 2 includes a box 2A, a lid 2B and a plurality of screws 2C, and stores the image generator 1.

The case 2 according to this embodiment has a rectangular panel shape.

(Box)

The box 2A constitutes a first component and includes a radiation incident part 21.

The box 2A according to this embodiment further includes side-face parts 22 (i.e. four side-face parts 22, which may be collectively referred to as a/the side-face part 22).

The box 2A according to this embodiment is electrically conductive. Examples of the method for making the box 2A electrically conductive include forming the box 2A with an electrically conductive material, such as a light metal or a CFRP resin. This can prevent discharge due to static electricity and suppress noise caused by static electricity.

The radiation incident part 21 constitutes a first part, and faces the third face 12b of the sensor panel 12 and spreads in parallel to the third face 12b. That is, the outer surface of the radiation incident part 21 is the radiation incidence plane.

The radiation incident part 21 according to this embodiment is formed so as to be a rectangular plate shape.

The radiation incident part 21 according to this embodiment is formed of a material that does not interfere with radiation transmission.

The side-face parts 22 constitute a third part, and extend from the peripheral portion of the radiation incident part 21 in a direction that is perpendicular to the third face 12b of the sensor panel 12 and in which the lid 2B is present.

That is, the surfaces of the side-face parts 22 are the side faces of the case 2.

The side-face parts 22 may be integrated with the radiation incident part 21, or may be separate from the radiation incident part 21.

Because the radiation incident part 21 according to this embodiment is rectangular as described above, as shown in FIG. 1, on an end of the side-face parts 22 that extend from the peripheral portion of the radiation incident part 21, the end being farthest from the radiation incident part 21, a rectangular frame-shaped end face 22a is formed.

In the end face 22a of the side-face parts 22, a plurality of screw holes 221 is formed.

Each screw hole 221 may be formed by embedding a female-screw-formed insert nut 221a in an embedment hole 22b formed in the side-face part(s) 22 (shown in FIG. 4), or may be formed by directly forming a female screw in the side-face part(s) 22 (shown in FIG. 5).

As shown in FIG. 3, each screw hole 221 is formed at a position that is not a position in a central portion 22c in the longer direction of each of the four side-face parts 22 disposed along the four sides of the radiation incident part 21.

It is preferable that the outermost layer of the box 2A be insulative. Examples of the method for making the outermost layer insulative include coating the surface of the box 2A, disposing a resin layer containing no fibers, and forming the box 2A with a metal that forms an oxide coating. This can prevent discharge due to static electricity and suppress noise caused by static electricity.

(Lid)

The lid 2B constitutes a second component and includes, as shown in FIG. 1 and FIG. 2, a second part 23.

As shown in FIG. 2, the second part 23 faces a fourth face 11b of the base 11 and spreads in parallel to the fourth face 11b.

The second part 23 according to this embodiment is formed of an electrically conductive material.

The second part 23 according to this embodiment is rectangular and has substantially the same size as the radiation incident part 21 of the box 2A.

As shown in FIG. 1, on the peripheral portion of the second part 23 (portion that is in contact with the end face 22a of the side-face parts 22 of the box 2A), at positions that coincide with the screw holes 221 of the side-face parts 22 when the lid 2B is placed on the box 2A, screw holes 23a are formed.

As with the box A2, it is preferable that the lid 2B be electrically conductive and the outermost layer thereof be insulative.

The lid 2B thus configured (component not having the third part) abuts the side-face parts 22 of the box 2A and is screwed to the side-face parts 22.

Hence, when the detector 100 is repaired or maintained, the lid 2B can be separated from the box 2A by only loosening and removing the screws 2C, and consequently the image generator 1 stored in the box 2A can be easily accessed.

The box 2A and the lid 2B according to this embodiment are electrically connected to one another via the screws 2C.

Hence, the case 2 as a whole functions as a shield against static electricity.

The electrical connection between the box 2A and the lid 2B may be performed by an electrically conductive adhesive or the like interposed between the box 2A and the lid 2B.

(Others)

As shown in FIG. 4, the lid 2B may include, for example, a reinforcing plate 24.

The reinforcing plate 24 is placed on the inner surface of the second part 23 so as to cover part of each screw hole 23a of the second part 23 to the extent that a shaft 26 of its corresponding screw 2C passes through the screw hole 23a and part of a head 25 of the screw 2C abuts (is caught by) the reinforcing plate 24.

In this instance, the diameter of each screw hole 23a is larger than the diameter of the head 25 of each screw 2C.

This can suppress bumpiness on the surface of the case 2 caused by the head(s) 25 of the screw(s) 2C. In particular, when the thickness of the head 25 in the axial direction is equal to or less than the thickness of the second part 23, the head 25 of the screw 2C does not protrude from the surface of the lid 2B.

When the second part 23 is electrically conductive as in this embodiment, and the lid 2B includes the reinforcing plate 24, the reinforcing plate 24 may be electrically conductive and electrically connected to the second part 23.

The electrical connection between the second part 23 and the reinforcing plate 24 may be performed on their contact surface, or when their contact surface is insulated (e.g. an oxide coating is formed thereon), may be performed by applying an electrically conductive paste 27 or the like so as to be in contact with both of them.

The case 2 may include waterproof packing 2D (elastic body).

The waterproof packing 2D is sandwiched between the end face 22a of the box 2A and the lid 2B so as to be slightly crushed.

The waterproof packing 2D has a shape of a rectangular frame that is along the inner contour of the rectangular frame-shaped end face 22a.

When the lid 2B includes the reinforcing plate 24, the waterproof packing 2D may be disposed, as shown in FIG. 4, between the end face 22a and the reinforcing plate 24.

This can prevent liquid (water, medicine, blood, etc.) from entering an inner space S of the case 2.

The case 2 may include, for example, screw cover(s) 2E as shown in FIG. 5.

Each screw cover 2E is disposed so as to cover the head 25 of its corresponding screw 2C, the head 25 being exposed from the screw hole 23a of the lid 2B screwed to the box 2A.

The screw cover 2E may be fitted into the screw hole 23a of the lid 2B, or may be bonded to the head 25 of the screw 2C.

This can keep a user from touching the screw 2C.

This can also keep liquid from adhering to and rusting the screw 2C.

The screw cover 2E may be formed such that at least its peripheral portion is curved from the center side to the edge side of the screw cover 2E in a direction in which the box 2A is present. This makes the screw cover 2E less likely to come off.

When the screw cover 2E is bonded to the head 25 of the screw 2C, it is preferable that the surface of the screw cover 2E be smooth. This can reduce frictional force that the screw cover 2E receives from a hand of a person, a bed or the like, and accordingly reduce frictional force that acts on the screw 2C to which the screw cover 2E is bonded, thereby preventing the screw 2C from loosening.

In FIG. 1 and FIG. 2, the first component is the box 2A that includes the side-face parts 22 (third part), but the second component may be a box that includes side-face parts. That is, in the case 2, the first component or the second component includes the third part.

Alternatively, both of the first component and the second component may include side-face parts.

In this embodiment, the components/parts or the like constituting the case 2 are electrically conductive, but at least one of them may not be electrically conductive.

[1-1-3. Cushions]

As shown in FIG. 1 and FIG. 2, cushions 3 are interposed between (i) the inner surface(s) of the side-face parts 22 of the case 2 and (ii) the image generator 1.

The cushions 3 may be formed of an elastic body, such as rubber or plastic foam, or may be formed of a thermoplastic elastomer (e.g. Hytrel®).

The cushions 3 according to this embodiment are interposed between the inner surface of the case 2 and the base 11.

More specifically, as shown in FIG. 2, the cushions 3 are interposed between (i) the inner surface(s) of the side-face parts 22 of the case 2 and (ii) a fifth face(s) 11c that is in contact with the first face 11a and the fourth face 11b of the base 11.

As shown in FIG. 6, the cushions 3 according to this embodiment are disposed at predetermined intervals so as to surround the image generator 1, for example.

The cushions 3 according to this embodiment are bonded to the fifth face 11c.

When, for example, as shown in FIG. 7, the box 2A includes projections 22d that project to the inner space S, it is possible that side faces of the image generator 1 (base 11) facing the projections 22d are made to abut the projections 22d, and the cushions 3 are interposed between (i) side faces of the image generator 1 opposite to the side faces that abut the projections 22d and (ii) their corresponding side-face parts 22.

In the first embodiment, no cushion 3 may be provided. (In the second embodiment, which will be described later, at least one cushion 3 needs to be provided.)

[1-1-4. Others]

As shown in FIG. 2, the detector 100 may include a spacer 4 interposed between the inner surface of the radiation incident part 21 of the case 2 and the image generator 1.

This can fill a gap between the radiation incident part 21 and the image generator 1, and increase strength of the detector 100 and protect the image generator 1.

The spacer 4 may be elastic (have a cushioning function). This can prevent an impact received by the case 2 from acting on the image generator 1.

As shown in FIG. 2, the detector 100 may include a pressing member(s) 5 interposed between the peripheral portion of the base 11 and the lid 2B.

This can prevent the sensor panel 12 from peeling from the base 11 and being damaged when the case 2 deforms (bends, becomes depressed, etc.).

[1-2. Structure to Screw Lid to Box]

Next, a structure to screw the lid 2B to the box 2A in the case 2 (specific structure to the first embodiment) will be described in detail.

Figure 8A:
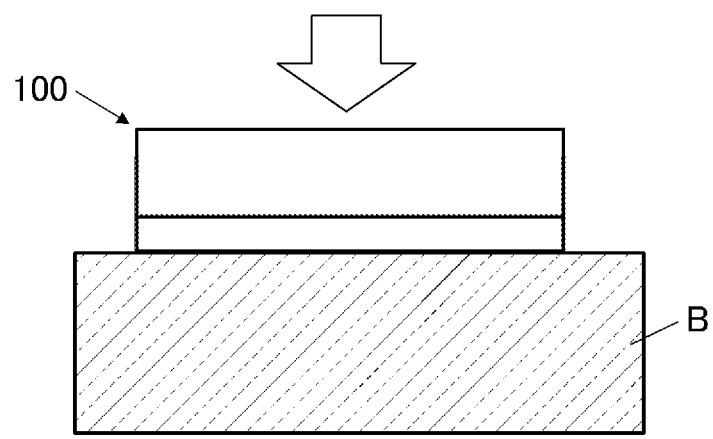
FIG. 8A and FIG. 8B are side views of the radiation detector according to the first embodiment placed on a bed.
Figure 8B:
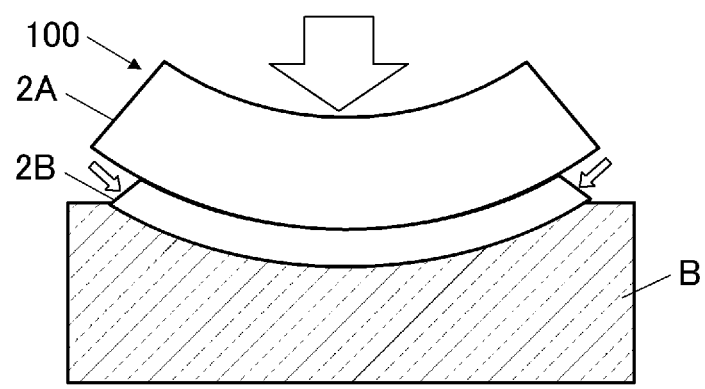
Figure 9A:
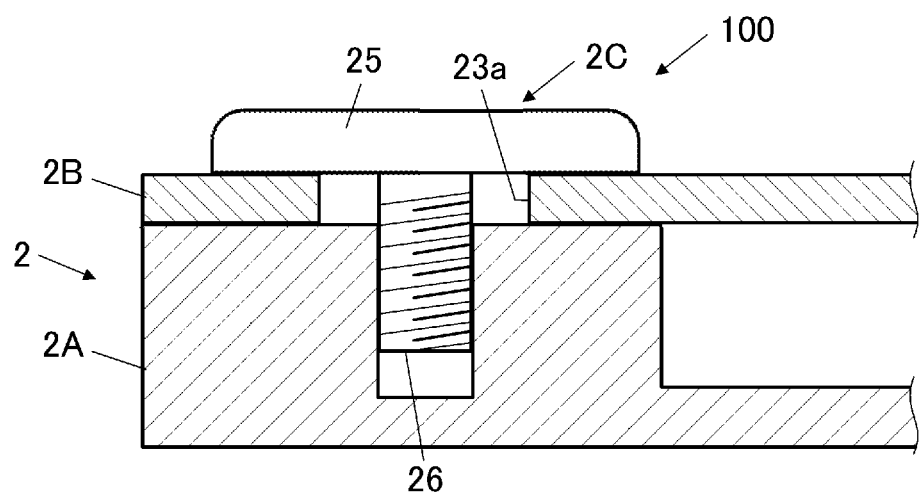
FIG. 9A and FIG. 9B are cross-sectional views of an end of the radiation detector according to the first embodiment cut in the thickness direction.
Figure 9B:
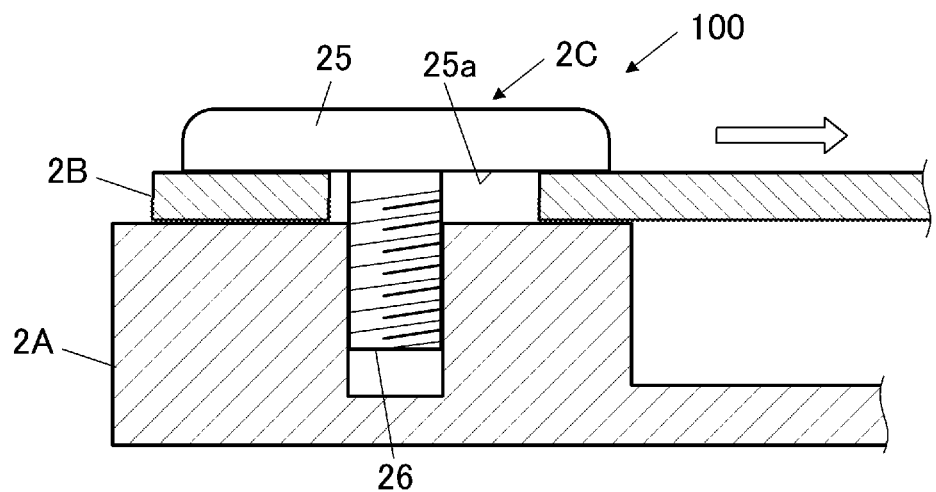
Figure 10:
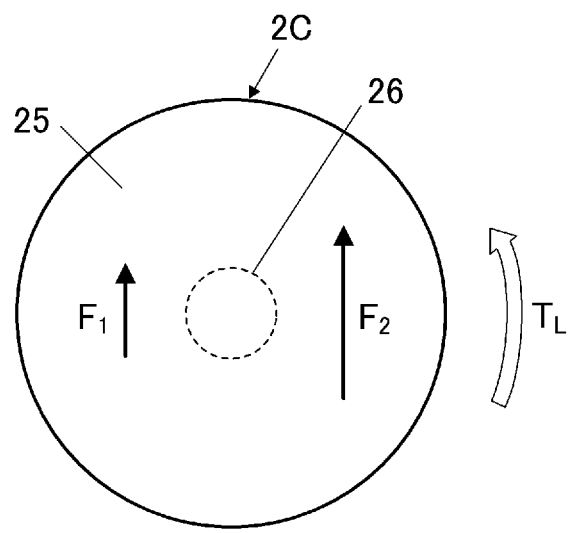
FIG. 10 is an illustration for explaining torque that acts on a screw(s)
Figure 11:
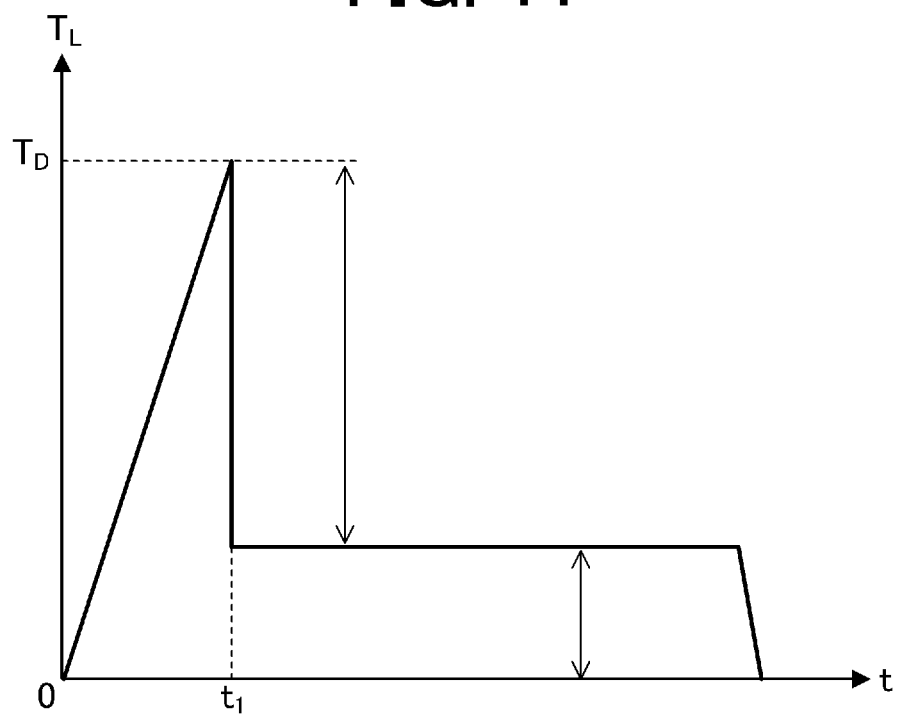
FIG. 11 is a graph showing temporal change of loosening torque $T_L$ that loosens a screw(s)

FIG. 8A and FIG. 8B are side views of the detector 100 placed on abed B. FIG. 9A and FIG. 9B are cross-sectional views of an end of the detector 100 cut in the thickness direction. FIG. 10 is an illustration for explaining torque that acts on the screw(s) 2C of the detector 100. FIG. 11 is a graph showing temporal change of loosening torque $T_L$ that loosens a screw(s). FIG. 12 to FIG. 15 are each a cross-sectional view of an end of an example of the detector 100 cut in the thickness direction.

[1-2-1. Regarding Looseness of Screws]

Examples of radiographic imaging using a panel-shaped radiation detector (detector 100 included) include, as shown in FIG. 8A, a method of placing a radiation detector on a bed or the like, laying an examinee thereon, and emitting radiation to the examinee from the above.

However, while the radiation incident plane of a radiation detector is planar, the body of an examinee has many curved surfaces. Hence, the contact surface of an examinee and a radiation detector is small. An examinee lying on a radiation detector therefore receives pressure from the radiation detector on their contact surface concentratedly and feels pain sometimes.

Then, in the case 2 of the detector 100, for example, as shown in FIG. 9A, the screw hole 23a of the lid 2B is formed such that its diameter is larger than the diameter of the shaft 26 of the screw 2C but smaller than the diameter of the head 25 of the screw 2C. This, as shown in FIG. 9B, makes the lid 2B movable with respect to the box 2A in a direction along the seat surface 25a of the screw 2C.

That is, as shown in FIG. 8B, both ends of the lid 2B slide from their corresponding ends of the box 2A, and accordingly the case 2 bends smoothly. As a result, the radiation incidence plane of the case 2 becomes a curved surface, so that the contact surface of the case 2 and an examinee lying on the radiation detector 100 becomes large, pressure that the examinee receives is dispersed, and consequently the examinee is less likely to feel pain.

In the case 2 thus configured, when the lid 2B moves with respect to the box 2A, the screw(s) 2C receives frictional force from the lid 2B.

At the time, if at least one of the seat surface 25a of the screw 2C and the surface of the lid 2B is not uniform (has minute bumpiness, etc.), and there is a difference (variation) in distribution of normal force that the screw 2C receives from the lid 2B or in distribution of a friction coefficient between the seat surface 25a of the screw 2C and the surface of the lid 2B, the frictional force that the screw 2C receives from the lid 2B may differ between one side and the other side of the shaft 26. More specifically, for example, as shown in FIG. 10, while the screw 2C receives frictional force $F_1$ from the lid 2B on the left side of the shaft 26, the screw 2C receives frictional force $F_2$ larger than the frictional force $F_1$ from the lid 2B on the right side of the shaft 26.

This difference in the frictional force is torque that acts in a direction to rotate the screw 2C (screw rotating direction). Depending on on which side of the shaft 26 the frictional force is larger, the difference may be "loosening torque $T_L$" that acts in a direction to loosen the screw 2C (screw loosening direction).

Incidentally, in the instance where a screw engaged with an object is loosened, for example, as shown in FIG. 11, as the loosening torque $T_L$ to be applied to the screw is increased, the screw starts to rotate in the screw loosening direction at a time $t_1$. The loosening torque $T_L$ of when the screw starts to loosen is "loosening start torque $T_D$".

Once the screw starts to loosen, the seat surface (25a) of the screw no longer receives frictional force from the object. As a result, the screw receives frictional force from the shaft (26) of the screw only, and hence loosens even by the loosening torque $T_L$ acting on the screw, the loosening torque $T_L$ being equal to the frictional force that the shaft 26 receives.

That is, when a radiation detector is placed on a bed or a sheet or the like laid on the bed, and the radiation detector is moved between an examinee and the bed or the like, the screw(s) of the radiation detector comes into contact with the bed or the sheet or the like on the bed, and the screw loosening progresses even by their friction.

If the screw(s) continues to loosen afterwards, the shaft thereof will eventually separate from the object and come out.

This phenomena is likely to occur, in particular, when, like a radiation detector, screws have a relatively small diameter and tightening torque cannot be made large, namely, when the loosening start torque $T_D$ cannot be made large.

In the detector 100, however, the loosening torque $T_L$ that acts on the screw 2C in the screw loosening direction when the seat surface 25a receives frictional force from the lid 2B is smaller than the loosening start torque $T_D$ that is the loosening torque $T_L$ of when the screw 2C starts to loosen.

That is, the detector 100 is configured such that the loosening torque $T_L$ that acts on the screw 2C when the case 2 bends does not reach the loosening start torque $T_D$.

The loosening torque $T_L$ that acts on the screw 2C is the sum of the frictional force that the head 25 of the screw 2C receives from the lid 2B and the frictional force that the shaft 26 of the screw 2C receives from the box 2A.

Hence, in order to prevent the loosening torque $T_L$ from reaching the loosening start Torque $T_D$, one of the following methods may be employed, for example.

Reduce the frictional force that the head 25 of the screw 2C receives from the lid 2B.

Increase the frictional force that the shaft 26 of the screw 2C receives from the box 2A.

[1-2-2. Reduction of Frictional Force That Head of Screw Receives From Lid]

Frictional force that one object receives from another object is obtained by multiplying a friction coefficient between these two objects by normal force that the one object receives from the other object.

Hence, in order to reduce the frictional force that the head 25 of the screw 2C receives from the lid 2B, one of the following methods may be employed, for example.

Reduce the normal force that the seat surface 25a receives from the lid 2B.

Reduce the friction coefficient between the surface of the lid 2B and the seat surface 25a.

(Reduction of Normal Force)

In order to reduce the normal force that the seat surface 25a receives from the lid 2B, compressive force that the head 25 of the screw 2C applies to the lid 2B is reduced.

In order to reduce the compressive force, in screwing, the seat surface 25a of the screw 2C is made to slightly come into contact with the lid 2B or to slightly separate from the lid 2B.

Examples of the method for performing screwing in this manner include a method using the insert nut 221a and a method using a stepped screw 2F.

Figure 12:
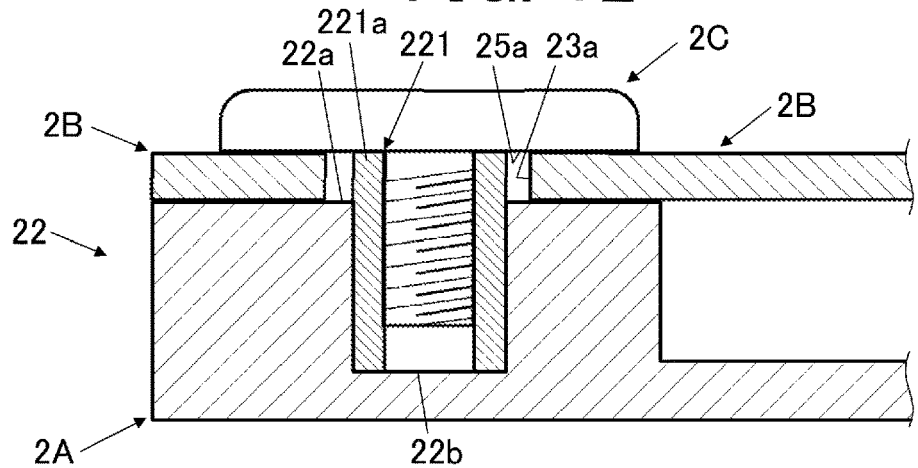
FIG. 12 is a cross-sectional view of an end of an example of the radiation detector according to the first embodiment cut in the thickness direction.

A cross section of an end of the detector 100 configured by employing the method using the insert nut 221a is, for example, as shown in FIG. 12.

That is, the insert nut 221a in this instance is embedded in the embedment hole 22b of the side-face part 22 of the box 2A such that the top of the insert nut 221a protrudes from the end face 22a of the side-face part 22 for a length equal to or greater than the thickness of the lid 2B.

The outer diameter of the insert nut 221a is smaller than the diameter of the screw hole 23a of the lid 2B.

It is preferable that the protruding length of the top be slightly greater than the thickness of the lid 2B.

The base (bottom) of the insert nut 221a may be in contact with the bottom of the embedment hole 22b, or may be positioned in the middle of the embedment hole 22b.

In the detector 100 thus configured, engagement of the screw 2C with the insert nut 221a is restrained from the point when the seat surface 25a of the screw 2C *comes* into contact with the top of the insert nut 221a, and hence the compressive force that the lid 2B receives from the seat surface 25a decreases. As a result, the normal force that the head 25 of the screw 2C receives from the lid 2B decreases.

In particular, when the protruding length of the top of the insert nut 221a is greater than the thickness of the lid 2B, the compressive force that the lid 2B receives from the seat surface 25a is negligibly small or zero. As a result, the normal force that the head 25 of the screw 2C receives from the lid 2B is negligibly small or zero.

The loosening torque $T_L$ that acts on the screw 2C as the lid 2B moves is based on the frictional force that the seat surface 25a of the screw 2C receives from the lid 2B, and hence is negligibly small.

On the other hand, the loosening start torque $T_D$ of the screw 2C is the sum of the frictional force that the seat surface 25a receives from the insert nut 221a and the frictional force that the shaft 26 of the screw 2C receives from the box 2A, and is larger than the loosening torque $T_L$.

Figure 13:
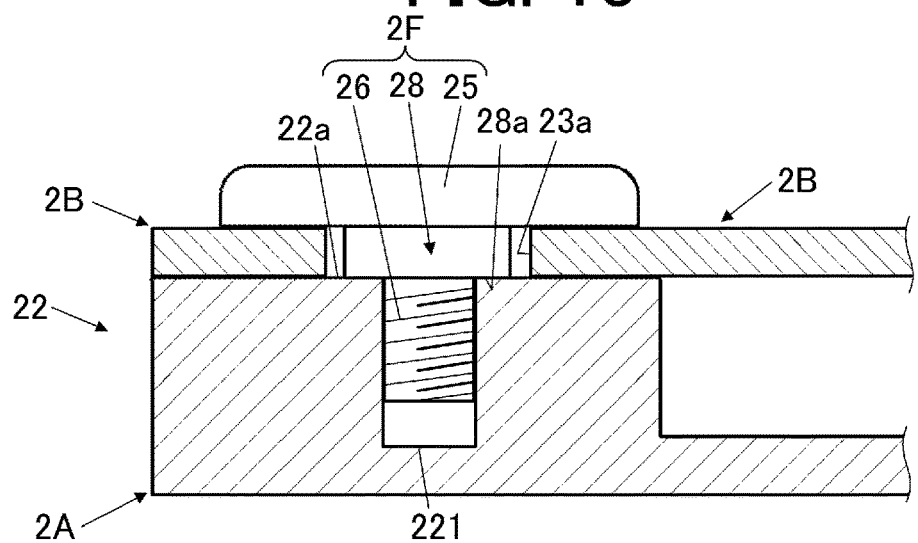
FIG. 13 is a cross-sectional view of an end of another example of the radiation detector according to the first embodiment cut in the thickness direction.

A cross section of an end of the detector 100 configured by employing the method using the stepped screw 2F is, for example, as shown in FIG. 13.

That is, the stepped screw 2F is configured such that the length of a step 28 in the axial direction, the step 28 being disposed between the head 25 and the shaft 26, is equal to or greater than the thickness of the lid 2B.

The diameter of the step 28 is smaller than the diameter of the screw hole 23a of the lid 2B.

Instead of the stepped screw 2F, a screw composed of the normal screw 2C the shaft 26 of which is inserted into a ring may be used, the ring having an outer diameter smaller than the diameter of the screw hole 23a of the lid 2B, an inner diameter equal to or larger than the diameter of the shaft 26 and a thickness equal to or greater than the thickness of the lid 2B.

In the detector 100 thus configured, engagement of the stepped screw 2F with the box 2A is restrained from the point when a second seat surface 28a of the step 28 of the stepped screw 2F comes into contact with the end face 22a of the box 2A, and hence, as in the instance where the insert nut 221a is used, the compressive force that the lid 2B receives from the seat surface 25a decreases. As a result, the normal force that the head 25 of the stepped screw 2F receives from the lid 2B decreases.

In particular, when the length of the step 28 in the axial direction is greater than the thickness of the lid 2B, the compressive force that the lid 2B receives from the seat surface 25a is negligibly small or zero. As a result, the normal force that the head 25 of the stepped screw 2F receives from the lid 2B is negligibly small or zero.

The loosening torque $T_L$ that acts on the stepped screw 2F as the lid 2B moves is, as in the instance where the insert nut 221a is used, negligibly small.

On the other hand, the loosening start torque $T_D$ of the stepped screw 2F is the sum of the frictional force that the second seat surface 28a of the step 28 receives from the box 2A and the frictional force that the shaft 26 of the stepped screw 2F receives from the box 2A, and is larger than the loosening torque $T_L$.

The detector 100 thus configured makes the normal force that the seat surface 25a of the screw 2C receives from the lid 2B fall within a range that makes the loosening torque $T_L$ smaller than the loosening start torque $T_D$.

(Reduction of Friction Coefficient)

Examples of the method for reducing the friction coefficient between the surface of the lid 2B and the seat surface 25a include a method using a washer(s) 2G and a method of performing surface treatment.

Figure 14:
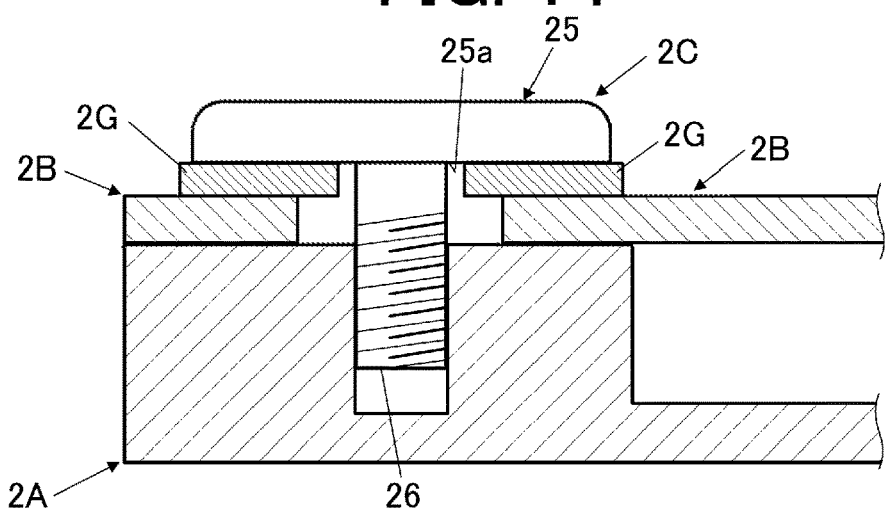
FIG. 14 is a cross-sectional view of an end of another example of the radiation detector according to the first embodiment cut in the thickness direction.

A cross section of an end of the detector 100 configured by employing the method using the washer 2G is, for example, as shown in FIG. 14.

That is, the washer 2G the surface of which is smoother than a smoother surface between the seat surface 25a and the surface of the lid 2B is interposed between the screw 2C and the lid 2B.

The washer 2G may not be perfectly ring-shaped, and hence may be partly cut off, like C-shaped.

Further, instead of using a single washer, a plurality of plate-like components may be disposed so as to surround the shaft 26.

The detector 100 thus configured, namely configured such that the washer 2G is interposed between the screw 2C and the lid 2B, can reduce at least one of the friction coefficient between the screw 2C and the washer 2G and the friction coefficient between the washer 2G and the lid 2B.

Hence, the frictional force that the head 25 of the screw 2C receives from the washer 2G is smaller than that in the instance where the washer 2G is not provided.

As a result, the loosening torque $T_L$ that acts on the screw 2C as the lid 2B moves is, as in the instance where the normal force that the head 25 receives is reduced, negligibly small.

On the other hand, the loosening start torque $T_D$ of the screw 2C is substantially the frictional force that the shaft 26 of the screw 2C receives from the box 2A, and is larger than the loosening torque $T_L$.

The detector 100 configured by employing the method of performing surface treatment is configured by performing surface treatment such that at least one of the surface of the lid 2B and the seat surface 25a of the screw 2C becomes smooth.

Examples of surface treatment include mirror finishing and coating with a PTFE (polytetrafluoroethylene) resin.

The detector 100 thus configured can reduce the friction coefficient between the screw 2C and the lid 2B by at least one of the seat surface 25a and the lid 2B being subjected to surface treatment.

Hence, the frictional force that the head 25 of the screw 2C receives from the lid 2B is smaller than that in the instance where surface treatment is not performed.

As a result, the loosening torque $T_L$ that acts on the screw 2C as the lid 2B moves is, as in the instance where the normal force that the head 25 receives is reduced, negligibly small.

On the other hand, the loosening start torque $T_D$ of the screw 2C is substantially the frictional force that the shaft 26 of the screw 2C receives from the box 2A, and is larger than the loosening torque $T_L$.

The detector 100 thus configured makes the friction coefficient between the box 2A and the shaft 26 of the screw 2C fall within the range that makes the loosening torque $T_L$ smaller than the loosening start torque $T_D$.

[1-2-3. Increase of Frictional Force That Shaft of Screw Receives From Box]

Examples of the method for increasing the frictional force that the shaft 26 of the screw 2C receives from the box 2A include a method using a screw anti-loosening agent 2H.

A cross section of an end of the detector 100 configured by employing the method using the screw anti-loosening agent 2H is, for example, as shown in FIG. 15.

That is, the screw anti-loosening agent 2H is interposed between the surface of the shaft 26 of the screw 2C and the wall surface of the screw hole 221 of the side-face part 22 of the box 2A. The screw anti-loosening agent 2H is applied to the surface of the shaft 26 or filled in the screw hole 221 before the screw 2C is fitted into (engaged with) the screw hole 221.

The screw anti-loosening agent 2H may be of a type that increases a friction coefficient between a male screw and a female screw, or of a type that adheres to a male screw and a female screw (that fixes the screw 2C to the screw hole 221), such as an anaerobic adhesive.

Which type of screw anti-loosening agent 2H is used is determined according to the magnitude of the loosening torque $T_L$ that acts on the screw 2C.

The detector 100 thus configured, namely configured such that the screw anti-loosening argent 2H is interposed between the surface of the shaft 26 and the wall surface of the screw hole 221, increases the friction coefficient between the screw 2C and the box 2A.

As a result, the frictional force that the shaft 26 of the screw 2C receives from the box 2A is larger than that in the instance where the screw anti-loosening agent 2H is not provided.

The loosening torque $T_L$ that acts on the screw 2C as the lid 2B moves is based on the frictional force that the head 25 receives from the lid 2B, and hence does not change between before and after the screw anti-loosening agent 2H is interposed as described above.

On the other hand, the loosening start torque $T_D$ of the screw 2C is the frictional force that the shaft 26 of the screw 2C receives from the box 2A, and is larger than that before the screw anti-loosening agent 2H is applied.

The detector 100 thus configured makes the frictional force that the shaft 26 of the screw 2C receives from the box 2A fall within the range that makes the loosening torque $T_L$ smaller than the loosening start torque $T_D$.

[1-2-4. Others]

Two or more of the above-described various methods for preventing the loosening torque $T_L$ from reaching the loosening start torque $T_D$ may be used in combination.

For example, the structure to screw the lid 2B to the box 2A may be combination of the insert nut 221a and the stepped screw 2F as shown in FIG. 16.

The structure to screw the lid 2B to the box 2A shown in FIG. 16 is the same as that shown in FIG. 4 except that the screw 2C is replaced by the stepped screw 2F.

In this instance, the engaging length of the shaft 26 with the insert nut 221a is shorter by the length of the step 28 of the stepped screw 2F in the axial direction. As a result, the crushed amount of the waterproof packing 2D is small, and reaction force that the lid 2B receives from the waterproof packing 2D (normal force that the stepped screw 2F receives from the lid 2B) decreases, so that the frictional force that the stepped screw 2F receives from the lid 2B (reinforcing plate 24) decreases.

The screw anti-loosening agent 2H may be interposed between the surface of the shaft 26 of the stepped screw 2F and the wall surface of the insert nut 221a.

Alternatively or additionally, the depth of the screw hole 221 of the box 2A and the length of the shaft 26 of the screw 2C/2F may be increased in order to lengthen time for the screw 2C/2F to come out when the screw 2C/2F loosens due to a factor(s) other than the frictional force that the screw 2C/2F receives from the lid 2B.

Alternatively or additionally, the thickness of the lid 2B may be increased in order to lengthen the time for the screw 2C/2F to come out when the screw 2C/2F loosens.

[1-3. Advantageous Effects]

The detector 100 according to the first embodiment described above has a configuration to have at least one of the following properties: the normal force that the screw 2C or the screw 2F receives from the lid 2B or the washer 2G is small; the friction coefficient between the screw 2C or the screw 2F and the lid 2B or the washer 2G is small; and the frictional force that the screw 2C or the screw 2F receives from the box 2A is large. This prevents the loosening torque $T_L$ that acts on the screw 2C/2F as the lid 2B moves, from reaching the loosening start torque $T_D$, and hence makes the screw 2C/2F less likely to loosen with movement of the lid 2B.

When a screw does not loosen, the head of the screw does not protrude from the surface of the lid, or the screw does not come out. As a result, the following situations do not occur: the protruding head of the screw catches an object or person therearound and scratches the object or person; the come-out screw adversely affects another device; and the come-out screw is accidentally swallowed by an examinee or the like and injures his/her health.

2. Second Embodiment

Next, a second embodiment according to the present disclosure will be described with reference to FIG. 1 to FIG. 7 and FIG. 17 to FIG. 23. However, the scope of the present invention is not limited to the embodiment below or illustrated examples.

[2-1. Schematic Configuration of Radiation Detector]

A schematic configuration of a radiation detector (hereinafter "detector 100A") according to the second embodiment is the same as that of the detector 100 according to the first embodiment except that the detector 100A needs to have at least one cushion 3.

In the second embodiment, the lid 2B may not be screwed to the box 2A.

Further, in the second embodiment, the case 2 does not need to be composed of the box 2A and the lid 2B. The case 2 may be a case including: a cylindrical body (third component) formed to be cylindrical by a radiation incident part (first part) that faces the third face 12b of the image generator 1 and spreads in parallel to the third face 12b, a back part (second part) that faces the fourth face 11b and spreads in parallel to the fourth face 11b, and a pair of side-face parts (third part) that connect both ends of the first part to both ends of the second part; and a lid (fourth component) that closes the opening of the cylindrical body.

[2-2. Structure to Prevent Cushion From Falling]

Next, a structure to prevent the cushion 3 from falling in the case 2 (specific structure to the second embodiment) will be described in detail.

Figure 17A:
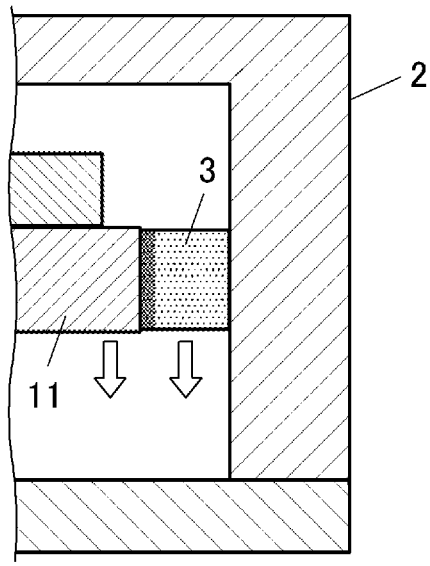
FIG. 17A and FIG. 17B are cross-sectional views of a conventional radiation detector cut in the thickness direction.
Figure 17B:
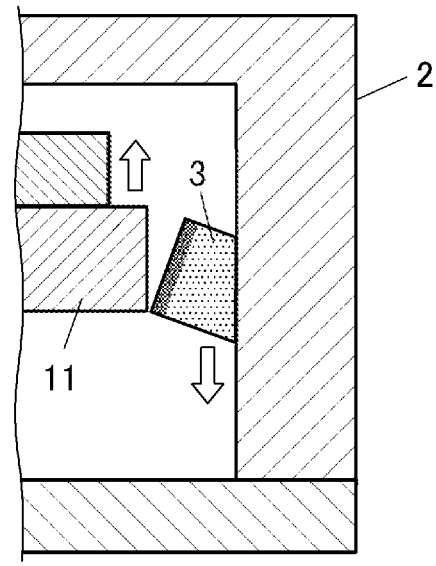

FIG. 17A and FIG. 17B are cross-sectional views of an end of a conventional radiation detector cut in the thickness direction. FIG. 18 to FIG. 23 each show one or two cross-sectional views of an end of an example of the detector 100A cut in the thickness direction.

[2-2-1. Falling of Cushion]

In the detector 100A, the cushion 3 is disposed between the image generator 1 and the inner surface(s) of the side-face part(s) 22 of the case 2 in order to keep an impact received from the outside from being transmitted to the sensor panel 12 or in order to position the sensor panel 12.

When the case 2 thus configured receives some kind of impact, the base may instantaneously deform and warp, and an end of the base may move in the thickness direction of the radiation detector.

In a conventional radiation detector, when the case thereof receives an impact, on the going trip, for example, as shown in FIG. 17A, the cushion moves together with the base, but, on the return trip, for example, as shown in FIG. 17B, the cushion receives, from the case, frictional force to stop the cushion's return, and thereby may fall from its position between the base and the case.

Even when the cushion is bonded to the base, the cushion may fall from the base by being deformed by (i) force to return the cushion to the original position received from the base and (ii) frictional force received from the case (by receiving force to separate the cushion from the base).

Then, the detector 100A includes, for example, a deformation restrainer (6, 7 or 8) shown in FIG. 18 to FIG. 23.

The deformation restrainer (6, 7 or 8) restrains the cushion 3 from deforming in a direction along the contact surface of the cushion 3 and the case 2.

Examples of the deformation restrainer according to this embodiment include a protrusion(s) 6, a rib(s) 7 and a friction reducer(s) 8.

(Protrusion)

The protrusion(s) 6 extends from the image generator 1 along the surface of the cushion 3.

Figure 18:
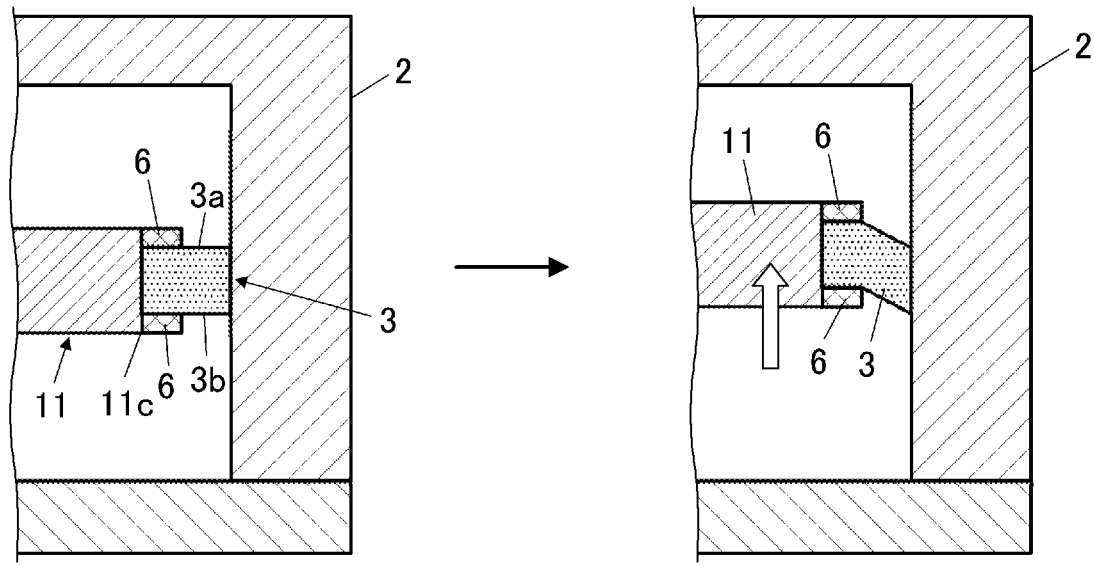
FIG. 18 shows cross-sectional views of an end of an example of the radiation detector according to the second embodiment cut in the thickness direction.

In this embodiment, the protrusions 6 extend, for example, as shown in FIG. 18, from both ends in the thickness direction of the fifth face 11c of the base 11 so as to be in contact with a sixth face 3a facing the radiation incident part 21 of the case 2 and a seventh face 3b opposite to the sixth face 3a of the cushion 3.

When the detector 100A thus configured receives an impact, an end of the base 11 moves and thereafter returns. At the time when the end of the base 11 returns, the protrusions 6 push the cushion 3 in a direction opposite to the direction of the frictional force received from the case 2. This restrains the cushion 3 from deforming in the direction along the contact surface of the cushion 3 and the case 2.

When, for example, as shown in FIG. 19, the side-face part 22 inclines from the thickness direction of the case 2, the protrusion 6 may be provided, of the both ends in the thickness direction of the fifth face 11c of the base 11, at only one end that has a longer distance from the side-face part 22 (where the cushion 3 is more likely to move; in FIG. 19, the seventh face 3b side).

The detector 100A including this protrusion 6 restrains the cushion 3 from deforming in the direction along the contact surface of the cushion 3 and the case 2 because the frictional force that the cushion 3 receives from the case 2 weakens at the time of movement in the easy movement direction when the end of the base 11 moves.

On the other hand, at the time of movement in the uneasy movement direction, the protrusion 6 pushes the cushion 3 in a direction opposite to the direction of the frictional force received from the case 2. This restrains the cushion 3 from deforming in the direction along the contact surface of the cushion 3 and the case 2.

The protrusions 6 may be provided, for example, as shown in FIG. 20A, at both ends in the thickness direction of the inner surface of the case 2 (side-face part 22).

When, for example, as shown in FIG. 20B, the side-face part 22 inclines from the thickness direction of the case 2, the protrusion 6 may be provided, of the both ends in the thickness direction of the inner surface of the case 2, at only one end that is closer to the end in the thickness direction of the fifth face 11c of the base 11 having a longer distance from the side-face part 22 (where the cushion 3 is more likely to move; in FIG. 20B, the seventh face 3b side).

As shown in FIG. 20C, the protrusion 6 may be integrated with the case 2 (box 2A).

When, as shown in FIG. 20D, the cushion 3 extends in the thickness direction of the case 2, because at least one of the radiation incident part 21 of the box 2A and the lid 2B restrains the cushion 3 from deforming in the direction along the contact surface of the cushion 3 and the case 2 (functions as a protrusion), no protrusion 6 may be provided.

(Rib)

Figure 21:
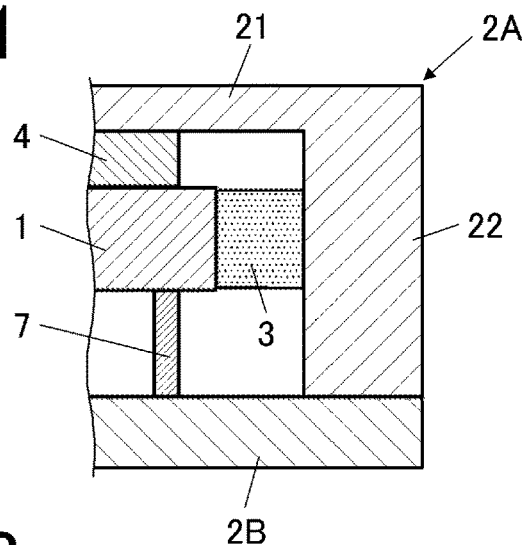
FIG. 21 is a cross-sectional view of an end of another example of the radiation detector according to the second embodiment cut in the thickness direction.

As shown in FIG. 21, the rib 7 extends from an end of the image generator 1 in the direction along the contact surface of the cushion 3 and the case 2.

The rib 7 according to this embodiment is disposed between the fourth face 11b of the base 11 and the lid 2B.

When the detector 100A having the rib 7 receives an impact, the rib 7 restrains the end of the base 11 from moving at least in a direction in which the rib 7 is present. Hence, the cushion 3 does not move at least in the direction in which the rib 7 is present, and does not receive frictional force from the case 2. This restrains the cushion 3 from deforming in the direction along the contact surface of the cushion 3 and the case 2.

The rib 7 may extend from the inner surface of the lid 2B or the inner surface of the radiation incident part 21 of the box 2A to the image generator 1.

The rib 7 may be integrated with the base 11, or may be integrated with the case 2 (lid 2B).

When the side-face part 22 inclines from the thickness direction of the case 2, the rib 7 may be provided, of the both ends in the thickness direction of the fifth face 11c of the base 11, at only one end that has a longer distance from the side-face part 22 (where the cushion 3 is more likely to move).

Further, the spacer 4 may be interposed between the inner surface of the radiation incident part 21 of the case 2 and the image generator 1.

(Friction Reducer)

Figure 22:
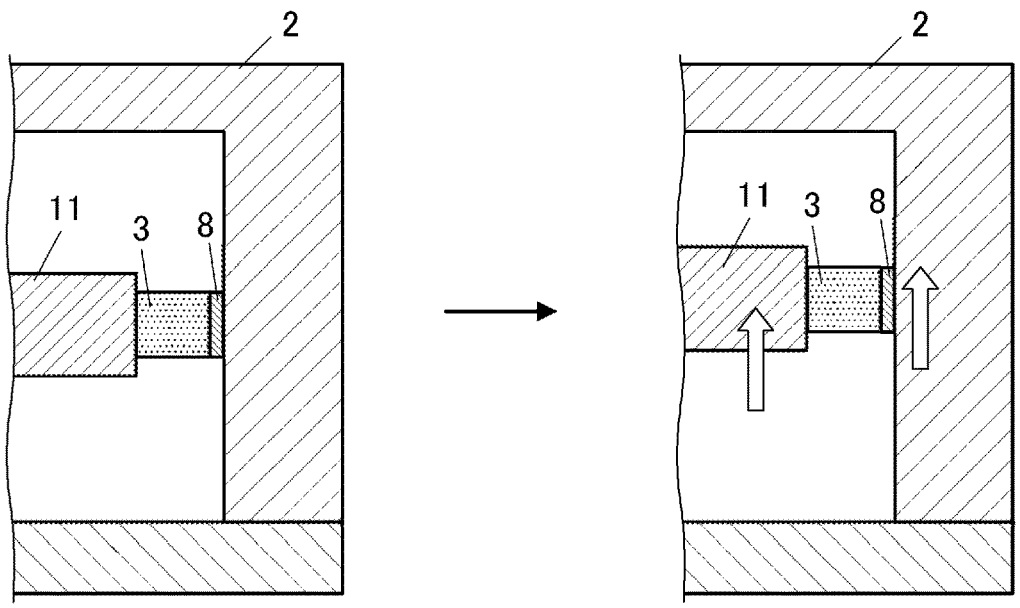
FIG. 22 shows cross-sectional views of an end of another example of the radiation detector according to the second embodiment cut in the thickness direction.

The friction reducer 8 is, for example, as shown in FIG. 22, interposed between the cushion 3 and the case 2.

The friction reducer 8 is composed of, for example, a film made of resin, and reduces the frictional force that the cushion 3 receives from the case 2.

Preferable examples of the resin that forms the film include a PET (polyethylene terephthalate) resin, polycarbonate resin and a fluororesin.

The friction reducer 8 according to this embodiment is fixed to the cushion 3 or the case 2.

Figure 23:
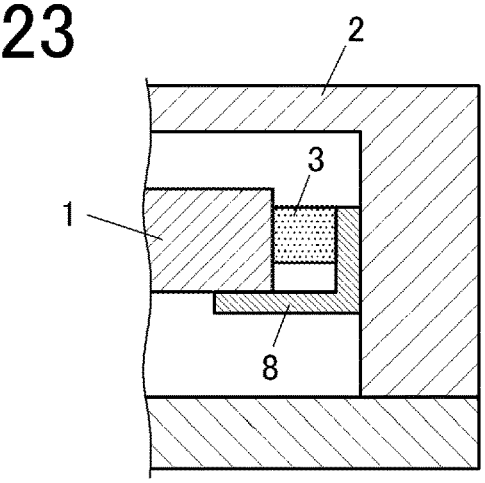
FIG. 23 is a cross-sectional view of an end of another example of the radiation detector according to the second embodiment cut in the thickness direction.

The friction reducer 8 may be configured, for example, as shown in FIG. 23, such that at least one of the both ends of the friction reducer 8 in the thickness direction of the case 2 extends to the image generator 1 (base 11).

[2-3. Advantageous Effects]

The detector 100A according to the second embodiment described above has a configuration to perform at least one of the following functions: restraining deformation of the cushion 3 caused by the frictional force received from the case 2; reducing the frictional force that the cushion 3 receives from the case 2; and restraining movement of the image generator 1 (base 11) that holds the cushion 3. This can prevent the cushion 3 from falling caused by an impact received by the case 2.

The cushion 3 not falling means the cushion 3 not moving in the case 2, and hence the cushion 3 does not adversely affect the functions of the detector 100A.

Although one or more embodiments of the present invention have been described and illustrated in detail, the disclosed embodiments are made for purposes of not limitation but illustration and example only. The scope of the present invention should be interpreted by terms of the appended claims

What is claimed is:

1. A radiation detector comprising:
an image generator that generates a radiograph according to received radiation; and
a case that stores the image generator and includes a first component and a second component screwed to the first component,
wherein the second component is movable with respect to the first component in a direction along a seat surface of a screw by a screw hole of the second component being formed such that a diameter is larger than a diameter of a shaft of the screw but smaller than a diameter of a head of the screw, and
wherein a loosening torque that acts, in a direction to loosen the screw, on the screw when the seat surface receives a frictional force from the second component is smaller than a loosening start torque that is the loosening torque of when the screw starts to loosen.

2. The radiation detector according to claim 1, wherein a normal force that the screw receives from the second component is within a range that makes the loosening torque smaller than the loosening start torque.

3. The radiation detector according to claim 2, further comprising an elastic body interposed between the first component and the second component.

4. The radiation detector according to claim 1, wherein a friction coefficient between the first component and the shaft is within a range that makes the loosening torque smaller than the loosening start torque.

5. The radiation detector according to claim 1, wherein a frictional force that the shaft receives from the first component is within a range that makes the loosening torque smaller than the loosening start torque.

6. The radiation detector according to claim 1,
wherein the image generator includes a plate-like base and a sensor panel disposed on a first face of the base,
wherein the sensor panel includes: a substrate; and a plurality of semiconductor elements formed so as to be two-dimensionally distributed on a third face of the substrate opposite to a second face of the substrate, the second face being in contact with the first face,
wherein the first component includes a first part that faces the third face of the sensor panel and spreads in parallel to the third face,
wherein the second component includes a second part that faces a fourth face of the base opposite to the first face and spreads in parallel to the fourth face,
wherein the first component or the second component includes a third part that extends in a direction perpendicular to the second face, and
wherein one of the first component and the second component not including the third part abuts the third part and is screwed to the third part.

* * * * *